United States Patent [19]

VandenBerg

[11] Patent Number: Plant 7,406

[45] Date of Patent: Dec. 25, 1990

[54] CHRYSANTHEMUM PLANT NAMED CONQUISTA

[75] Inventor: Cornelis P. VandenBerg, Salinas, Calif.

[73] Assignee: Yoder Brothers, Inc., Barberton, Ohio

[21] Appl. No.: 435,818

[22] Filed: Nov. 14, 1989

[51] Int. Cl.[5] ..... A01H 5/00

[52] U.S. Cl. ..... Plt./78

[58] Field of Search ..... Plt./78

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Conquista particularly characterized by its pompon capitulum form; formal decorative capitulum type; yellow ray floret color; diameter across face of capitulum of up to 6 cm at maturity; uniform eight week photoperiodic flowering response to short days; peduncle length ranging from 10 to 15 cm on open, terminal sprays; short plant height when grown as a single stem spray cut mum; and excellent tolerance to low temperatures for bud initiation and flower development.

3 Drawing Sheets

1

The present invention comprises a new and distinct cultivar of Chrysanthemum, botanically known as *Dendranthema grandiflora,* and referred to by the cultivar name Conquista.

Conquista, identified as 85-877003, was originated from a cross made by Cornelis P. VandenBerg in a controlled breeding program in Salinas, Calif., in 1984.

The female parent of Conquista was the cultivar identified as Butterball, disclosed in U.S. Plant Pat. No. 4,556. The male parent of Conquista was an unnamed seedling identified as 79-C08001, and described as a golden bronze decorative spray cut mum with tall plant height and nine week photoperiodic flowering response.

Conquista was discovered and selected as one flowering plant within the progeny of the stated cross by Cornelis P. VandenBerg in September 1985, in a controlled environment in Salinas, Calif.

The first act of asexual reproduction of Conquista was accomplished when vegetative cuttings were taken from the initial selection in November 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Conquista are firmly fixed and are retained through successive generations of asexual reproduction.

Conquista has not been observed under all possible environmental conditions. The phenotype may vary significantly with variations in environment such as temperature, light intensity and daylength.

The following observations, measurements and comparisons describe plants grown in Salinas, Calif., under greenhouse conditions which approximate those generally used in commercial greenhouse practice. The low temperature tolerance of the new variety as noted below was determined in repeated flowerings in Bogota, Colombia.

The following traits have been repeatedly observed and are determined to be basic characteristics of Conquista, which, in combination, distinguish this Chrysanthemum as a new and distinct cultivar:

2

1. Pompon capitulum form.
2. Formal decorative capitulum type.
3. Yellow ray floret color.
4. Diameter across face of capitulum of up to 6 cm at maturity.
5. Uniform eight week photoperiodic flowering response to short days.
6. Peduncle length ranging from 10 to 15 cm on open, terminal sprays.
7. Short plant height, requiring two to three long day weeks prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Conquista, with the colors being as nearly true as possible with illustrations of this type. Sheet 1 is a color photograph of Conquista grown as a single stem cut spray mum. Sheet 2 is a black and white photograph of three views of the inforescence of Conquista. Sheet 3 is a black and white photograph showing the upper and under sides of the leaves of Conquista at three stages of development (mature, intermediate and immature).

Of the commercial cultivars known to the inventor, the most similar in comparison to Conquista is the cultivar identified as Gleam, disclosed in U.S. Plant Pat. No. 5,713. Reference is made to attached Chart A, which compares certain characteristics of Conquista to the same characteristics of Gleam.

Similar traits are ray floret color (although the florets of Conquista are somewhat more golden), capitulum form and type, and spray formation. Conquista has shorter peduncles, smaller diameter of capitulum (6 cm. compared to 7 cm. at fully maturity), shorter plant height, earlier flowering response, and better tolerance to low temperatures than Gleam. The improved tolerance to low temperatures has been determined under night growing conditions in Bogota, Colombia, which can reach as low as 5°-10° C. At such temperatures, plant of Gleam frequently exhibit very uneven and delayed flowering, and occasionally no flowering at all. By comparison, at the same temperatures plants of Conquista maintain very uniform flowering.

In the following description color references are made to The Royal Horticultural Society Color Chart. The color values were determined on plant material grown in Salinas, Calif. on July 14, 1989.

Classification:

*Botanical.*—*Dendranthema grandiflora* cv Conquista.

*Commercial.*—Formal decorative cut spray mum.

INFLORESCENCE

A. Capitulum:

*Form.*—Pompon.

*Type.*—Formal decorative.

*Diameter across face.*—Up to 6 cm at maturity.

B. Corolla of ray florets:

*Color (general tonality from a distance of three meters).*—Yellow.

*Color (upper surface).*—9A to 9B. The center of the flowers shows a green overcost.

*Color (under surface).*—6A to 6B.

*Shape.*—Straight, cross-section concave.

C. Corolla of disc florets:

*Color (mature).*—Closest to 154B.

*Color (immature).*—Closest to 144C.

D. Reproductive organs:

*Androecium.*—Present on disc florets only; very few disc florets, not visible in the mature flower; no pollen.

*Gynoecium.*—Present on both ray and disc florets.

PLANT

A. General appearance:

*Height.*—Short; 90 to 100 cm as a single stem cut mum with two to three long day weeks prior to short days.

B. Foliage:

*Color (upper surface).*—147A.

*Color (under surface).*—147B.

*Shape.*—Very deeply lobed, slightly serrated.

CHART A

COMPARISON OF CONQUISTA AND GLEAM

| | CONQUISTA | GLEAM |
|---|---|---|
| Ray floret color | Yellow | Yellow |
| Capitulum form and type | Pompon<br>Formal decorative | Pompon<br>Formal decorative |
| Spray formation | Terminal | Terminal |
| Peduncle length | 10 to 15 cm | 20 to 35 cm |
| Diameter across face of Capitulum | Up to 6 cm | Up to 7 cm |
| Plant height | Short | Medium |
| Flowering response period | 8 weeks | 9 weeks |
| Low temperature tolerance | Excellent | Marginal |

Comparisons Made of Plants Grown As Single Stem Spray Cut Mums In Salinas, California

I claim:

1. A new and distinct Chrysanthemum plant named Conquista, as described and illustrated.

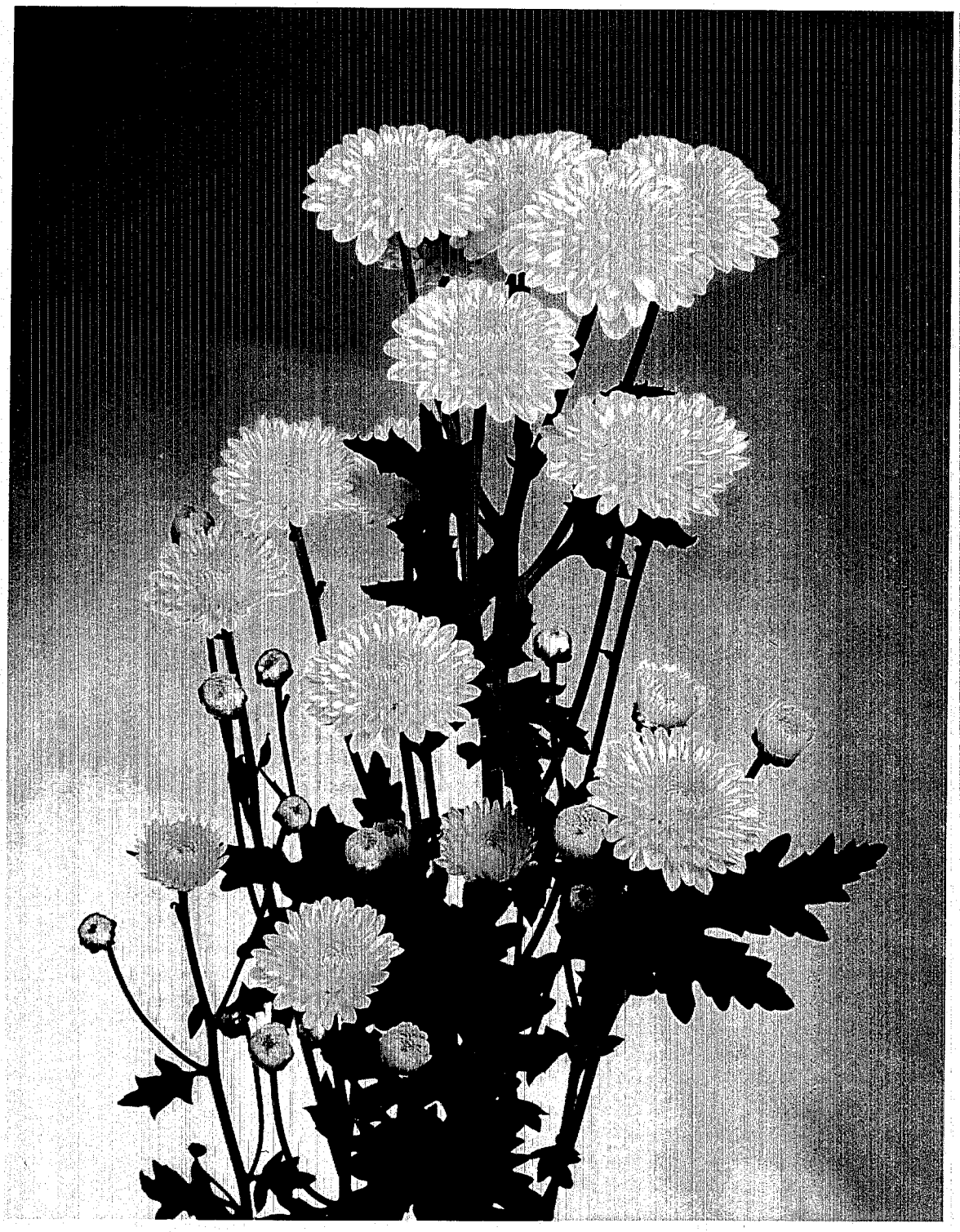

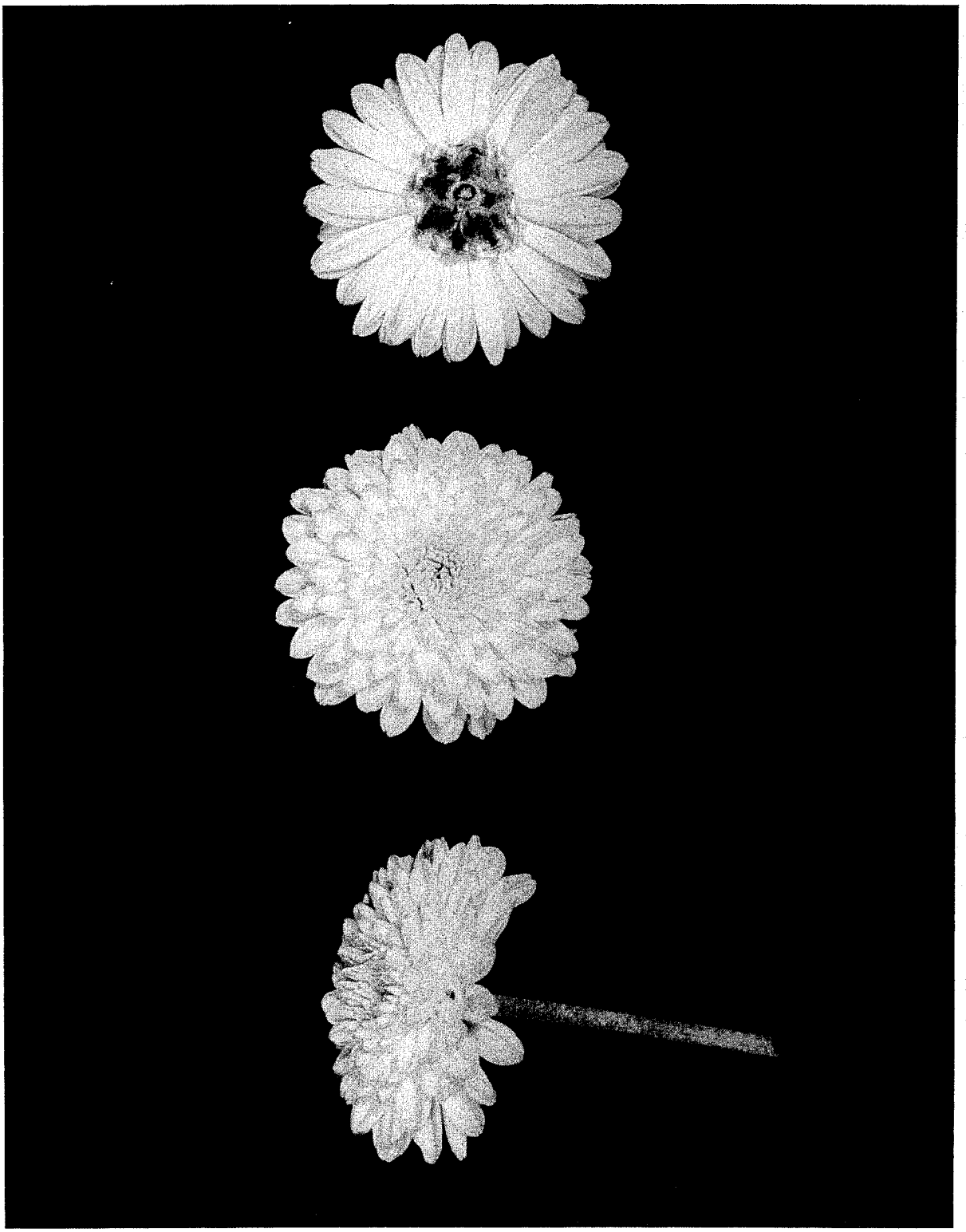

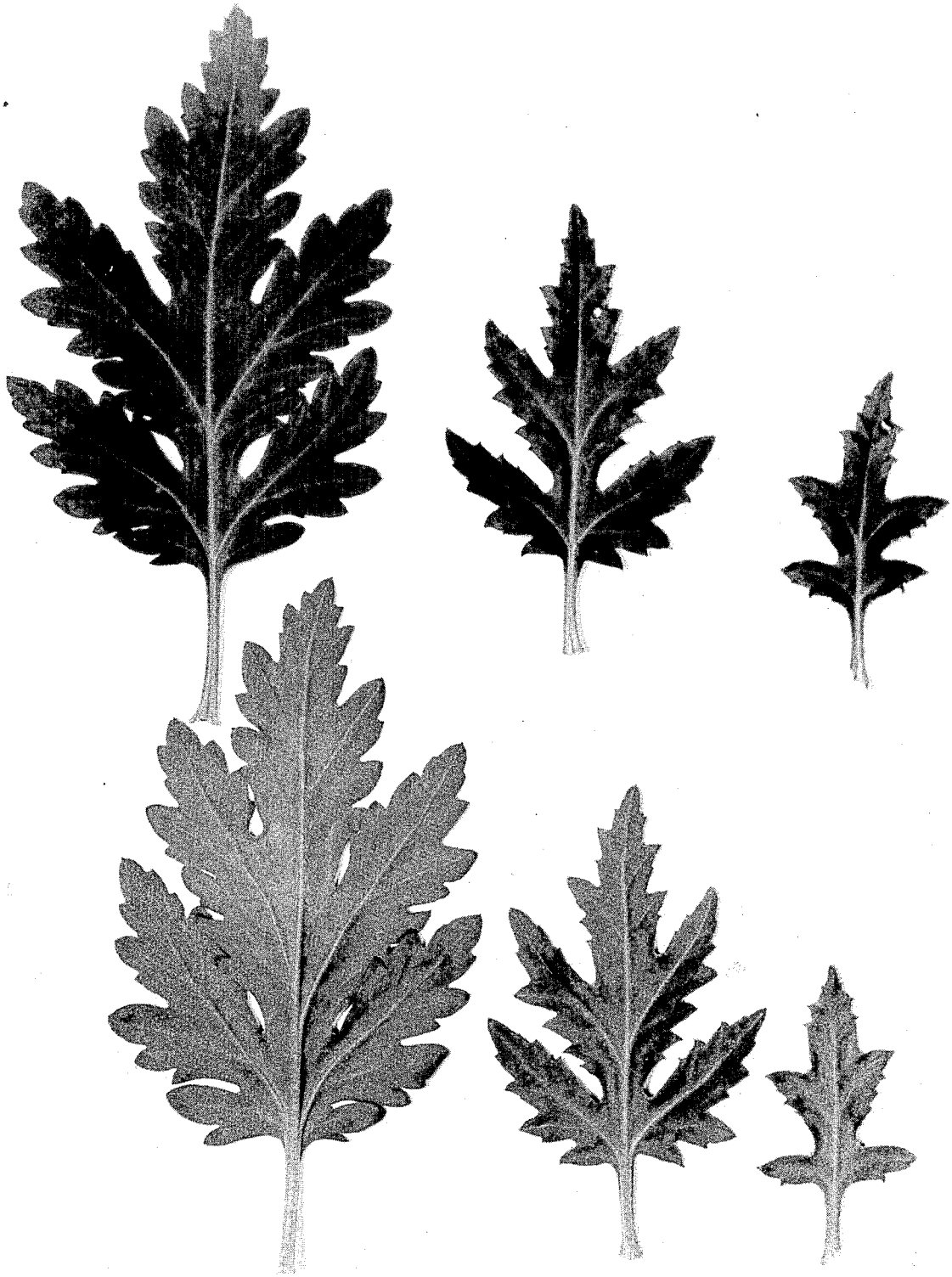

* * * * *